(12) United States Patent
Gorka

(10) Patent No.: US 8,246,239 B2
(45) Date of Patent: Aug. 21, 2012

(54) METHOD OF METERING AND MIXING

(75) Inventor: Guenther Gorka, Bad Camberg (DE)

(73) Assignee: DiaSys Diagnostic Systems GmbH (DE)

( * ) Notice: Subject to any disclaimer, the term of this patent is extended or adjusted under 35 U.S.C. 154(b) by 421 days.

(21) Appl. No.: 12/226,122

(22) PCT Filed: Apr. 11, 2007

(86) PCT No.: PCT/EP2007/053525
§ 371 (c)(1),
(2), (4) Date: Feb. 20, 2009

(87) PCT Pub. No.: WO2007/116083

PCT Pub. Date: Oct. 18, 2007

(65) Prior Publication Data
US 2009/0316519 A1 Dec. 24, 2009

(30) Foreign Application Priority Data
Apr. 11, 2006 (DE) .......................... 10 2006 017 360

(51) Int. Cl.
*G01N 35/10* (2006.01)
*B01F 11/00* (2006.01)
(52) U.S. Cl. .......................... 366/137; 366/269; 366/348
(58) Field of Classification Search .................. 366/131, 366/136, 137, 163.1, 164.1, 164.2, 191, 261, 366/267, 269, 348, 349; 99/346
See application file for complete search history.

(56) References Cited

U.S. PATENT DOCUMENTS

| 3,831,816 | A | * | 8/1974 | Pauliukonis | 222/135 |
| 4,574,850 | A | * | 3/1986 | Davis | 141/9 |
| 5,015,591 | A | * | 5/1991 | Meyrat et al. | 436/178 |
| 5,133,392 | A | | 7/1992 | Hamann | |

(Continued)

FOREIGN PATENT DOCUMENTS
DE 31 15 568 A1 4/1980
(Continued)

OTHER PUBLICATIONS

English Language Translation of International Preliminary Report on Patentability, Nov. 17, 2008, PCT.

*Primary Examiner* — Yogendra Gupta
*Assistant Examiner* — Emmanuel S Luk
(74) *Attorney, Agent, or Firm* — Gerald K. White

(57) ABSTRACT

The invention concerns a method of automatically metering and mixing liquids effectively as quickly as possible and in few steps. The following steps: a) dispensing the liquid from a needle into the vessel, wherein the operation begins when the needle is at starting position (S), the dispensing operation is continued while the needle is moved in a vertical direction down toward end position (E), wherein the starting position is at a spacing from the bottom of the vessel; b) sucking up a part of the liquid present in the vessel while the needle is in the end position (E); c) moving the needle in a vertical direction to the starting position (S); and d) dispensing the liquid from the needle, wherein the dispensing begins when the needle is at starting position (S), dispensing operation is continued while the needle is moved in a vertical direction downwardly in the direction of the end position (E), and dispensing operation ends when the needle is at end position (E).

20 Claims, 2 Drawing Sheets

U.S. PATENT DOCUMENTS

Figure 1:
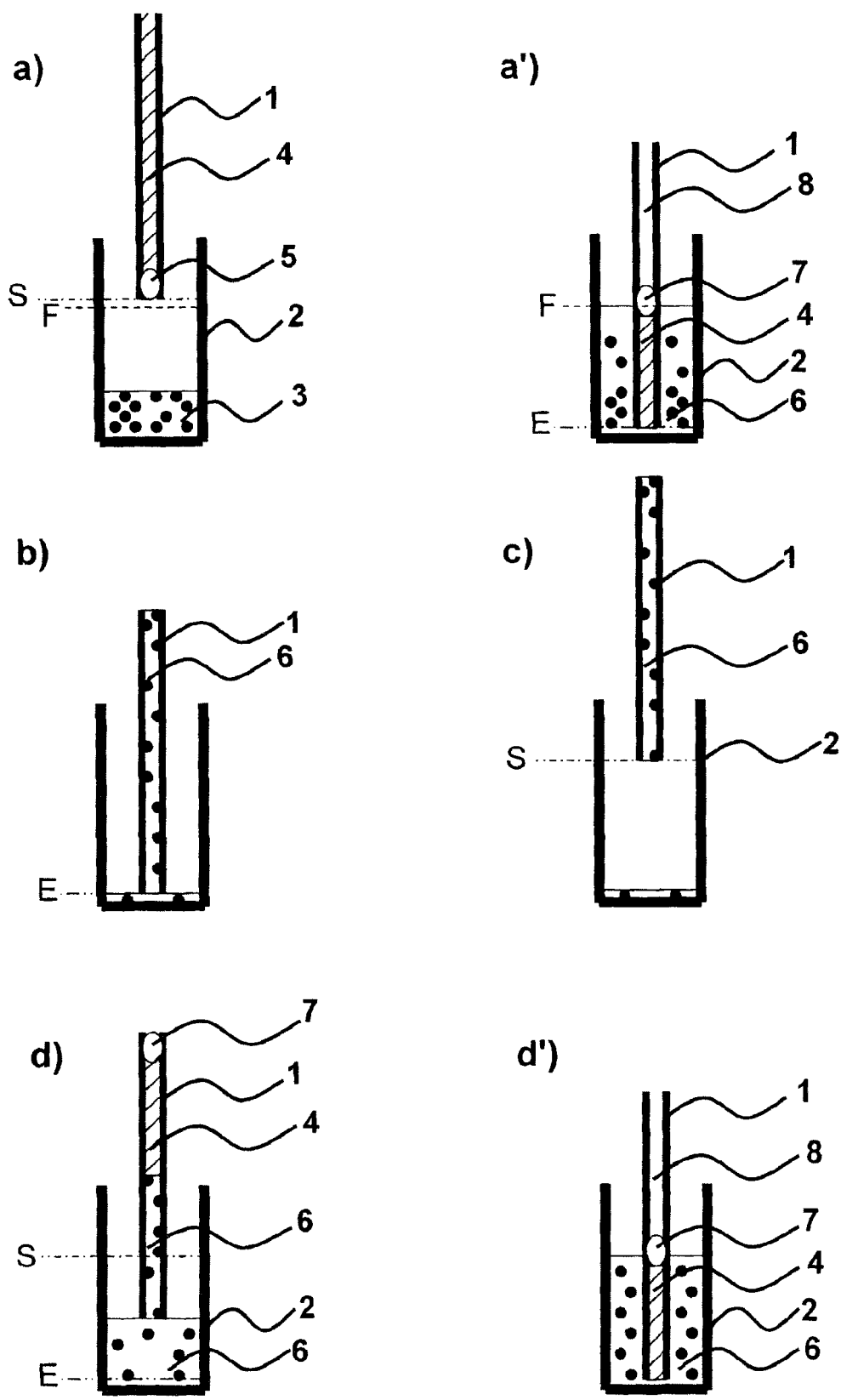

| | | | |
|---|---|---|---|
| 5,452,619 A * | 9/1995 | Kawanabe et al. | 73/864.01 |
| 5,555,767 A * | 9/1996 | Makino et al. | 73/863 |
| 6,063,635 A * | 5/2000 | Ohta et al. | 436/54 |
| 6,685,693 B1 * | 2/2004 | Casso | 604/500 |
| 6,869,571 B2 * | 3/2005 | Ingenhoven et al. | 422/510 |
| 7,125,727 B2 * | 10/2006 | Massaro | 436/180 |
| 7,621,892 B2 * | 11/2009 | Fago et al. | 604/151 |

FOREIGN PATENT DOCUMENTS

| | | |
|---|---|---|
| EP | 1498736 | 1/2005 |
| EP | 1138372 | 7/2008 |
| WO | WO 93/25309 | 12/1993 |

* cited by examiner

METHOD OF METERING AND MIXING

The present invention concerns a method of automatically metering and mixing liquids in a sample vessel by means of a metering needle.

Automatic or semi-automatic implementation of chemical reactions, in particular analysis methods, requires a plurality of liquids such as samples and reagents to be homogeneously mixed. The most frequently employed method provides that, after the addition of all liquids, a mixing device is introduced into the reaction vessel and the liquids are mixed by stirring. That method suffers from the disadvantage that there is an additional component which has to be programmed and the risk of contamination is increased by an additional instrument which comes into contact with the liquids.

JP 07239334 describes a further method of mixing liquids in which a small amount of a first sample solution is pipetted into the sample vessel and then a large amount of a diluting solution is added with a further pipette. That method is only suitable if two liquids of very different volumes are to be mixed. Moreover that method cannot provide for homogeneous mixing for every kind of liquids.

A further method of mixing liquids by means of a pipette is described in JP 62184357. In that case a pipette or metering needle is immersed a plurality of times in the liquid in a sample vessel, the liquid is sucked up, thereafter the pipette is raised so that the tip thereof is above the surface of the liquid and the liquid is expelled again. That method has to be frequently repeated to achieve homogeneous mixing.

Taking that state of the art as its basic point, the object of the present invention is to provide a method of automatically metering and mixing liquids, wherein the liquids are particularly effectively mixed as quickly as possible and in few steps, which is simple to carry out and inexpensive and which does not require any additional component.

That object is attained by a method of the kind set forth in the opening part of this specification, which comprises the following steps:

a) dispensing a volume of a liquid or a plurality of volumes of a plurality of liquids from a metering needle into a sample vessel, wherein the operation of dispensing the liquid or liquids from the metering needle begins when the dispensing opening of the metering needle is at a starting position (S), the dispensing operation is continued while the metering needle is moved in a vertical direction downwardly in the direction of an end position (E), and the dispensing operation ends when the dispensing opening of the metering needle is at the end position (E), wherein the starting position is disposed in a vertical direction at a spacing from the bottom of the sample vessel, which corresponds to the maximum filling height of the sample vessel after complete dispensing of the liquid in this step or is above said filling height or at a maximum 10% therebelow, with respect to the spacing from the bottom of the sample vessel to the maximum filling height of the sample vessel after complete dispensing of the liquid in this step, and wherein the end position (E) is in a vertical direction beneath the starting position (S) and at a spacing relative to the bottom of the sample vessel;

b) sucking up at least a part of the volume of liquid present in the sample vessel by means of the metering needle while the dispensing opening of the metering needle is in the end position (E);

c) moving the metering needle in a vertical direction until the dispensing opening is at the starting position (S); and d) dispensing the volume of liquid which has been sucked up from the dispensing needle, wherein the dispensing operation begins when the dispensing opening of the metering needle is at the starting position (S), the dispensing operation is continued while the metering needle is moved in a vertical direction downwardly in the direction of the end position (E), and the dispensing operation ends when the dispensing opening of the metering needle is at the end position (E).

A preferred method is one in which prior to step a) a volume of a liquid or a plurality of volumes of a plurality of liquids are dispensed from a metering needle into the sample vessel. In that way for example one or more samples, reagents or buffers can be presented in different sample vessels and the actual mixing operation is effected with the addition of a further liquid.

A further preferred method is one in which steps a) to d) are repeated with one or more liquids. In many cases chemical reactions are controlled by the addition of a given substance. Particularly in analytical reactions therefore it is necessary for that substance to be mixed with the other liquids as quickly as possible to ensure a unitary reaction. The method according to the invention makes it possible to achieve rapid homogeneous mixing of all liquids.

A preferred method in accordance with the invention is also one in which steps b) to d) are repeated one or more further times. Many liquids can be only very slowly pipetted by virtue of their physical properties such as viscosity, and possibly mix very poorly with other liquids, it is therefore desirable if the steps of sucking up and re-dispensing the liquid into the sample vessel are repeated. In that way homogeneous mixing is achieved even with liquids involving high levels of viscosity, very different viscosities or very different densities.

A particularly preferred method is one in which the starting position (S) is in a vertical direction at a spacing above the maximum filling height after complete dispensing of the liquid in the respective step, of between 0.5% and 50%, preferably between 0.5% and 20%, with respect to the spacing from the bottom of the sample vessel to the maximum filling height of the sample vessel after complete dispensing of the liquid in the respective step. The starting position at which the metering needle is disposed at the beginning of the operation of dispensing the liquid is to be above the filling height of the sample vessel after complete dispensing of the liquid as a plurality of successively added liquids or a liquid which is already present already mix with the liquids which are added, due to the turbulence effects which occur when the liquid encounters the surface of the liquid. If the spacing is excessively small, sufficient turbulence effects do not occur, while if it is too great, there is the risk that a part of the added liquid remains at the edge of the sample vessel or splashing occurs when the liquid encounters liquid which is already present, and that would result in a loss of liquids and thus inaccuracies.

A further preferred method is one in which the end position (E) is in a vertical direction at a spacing above the bottom of the sample vessel, of between 0.5% and 20%, preferably between 0.5% and 10%, particularly preferably between 0.5% and 5%, with respect to the spacing from the bottom of the sample vessel to the maximum filling height of the sample vessel after complete dispensing of liquid in the respective step. The end position of the dispensing opening of the metering needle is to be clearly below the maximum filling height of the sample vessel so that the major part of the dispensing operation takes place beneath the surface of the liquid and that therefore ensures thorough mixing of the liquids in a vertical direction.

On the other hand it is necessary for a minimum spacing to be maintained between the dispensing opening of the metering needle and the bottom of the sample vessel so that it is possible to suck up liquid, in the end position.

It is further preferred if, in a method according to the invention, a plurality of liquid volumes are separated in the metering needle by air bubbles. Those separation air bubbles prevent mixing of the liquid in the metering needle, thereby preventing an uncontrolled reaction and contamination of the liquids. Preferably the separation air bubbles are dispensed from the metering needle above the surface of the liquid so that, after dispensing of the liquid, no air bubbles remain in the volume of liquid in the sample vessel, which could otherwise interfere with possible measurements.

A particularly preferred method is one in which before step b) the metering needle is displaced in a vertical direction upwardly until the dispensing opening is above the surface of the liquid, then a separation air bubble is sucked in and then the metering needle is moved into the end position (E) again. To achieve an exact added volume, more liquid can be contained in the metering needle, than is to be added. The addition operation is stopped when the desired volume has been dispensed into the sample vessel from the metering needle. Accordingly, a part of a liquid which is not to be mixed with the liquids in the sample vessel remains in the metering needle. The fact that a separation air bubble is sucked in, after step a), prevents the liquids which are already in the sample vessel and which are to be mixed or which are already mixed from becoming mixed in the subsequent steps with the liquid which remains in the metering needle.

A preferred method is also one in which the speed at which the metering needle is moved into the sample vessel is proportional to the speed of dispensing of the liquid or liquids. The starting position (S) and the end position (E) represent at the same time the starting and end points of a movement and the starting and end points of dispensing of the liquid. If the two speeds are proportional to each other, calculation of the speeds is simplified.

A further preferred method is one in which the speed at which the metering needle is moved into the sample vessel and/or the speed of dispensing of the liquid or liquids from the metering needle remains constant. Speeds which remain constant, both for dispensing and also the speed at which the metering needle is moved into the sample vessel, guarantee uniform distribution of the liquids which are dispensed, particularly when the metering needle is beneath the surface of the liquid. Moreover speeds which remain constant are also easier to implement in an automation procedure.

A further preferred method is one in which the speed of dispensing of the liquid or liquids from the metering needle is between 0.1 and 2 ml/s, preferably between 0.2 and 1 ml/s. For total volumes of typically up to 1 ml, those are suitable dispensing speeds so that homogeneous mixing is achieved in as few steps as possible. Higher speeds can result in liquid being splashed and sprayed out and thus result in volume errors in dispensing liquid, and that would not guarantee unitary reaction conditions. Lower speeds in dispensing the liquid would not afford sufficient turbulence so that a less good mixing effect results therefrom and therefore additional repetitions of steps b) to d) would be required, which additionally slows down the method.

A particularly preferred method is one in which in step b) 50-100% by volume of the volume of liquid present in the sample vessel, preferably 70-95% by volume, particularly preferably 90-95% by volume, is sucked up. If less than 50% by volume of the volume of liquid is sucked up, then the number of mixing operations required to achieve homogeneous mixing is increased. Sucking up more than 95% by volume is technically not appropriate as the probability that air would also be sucked in that situation is very great and that would not guarantee better mixing.

It is also particularly preferred if the metering needle is used for temperature control of the liquids. A large surface area of liquid comes into contact with the metering needle in the operation of sucking up and dispensing liquids, it is appropriate to heat the metering needle and thereby provide for rapid preliminary temperature control of the liquid. That also reduces the demands on further technical equipment which serves for temperature control of the liquids, whereby the method becomes less expensive.

A further preferred method is one in which a metering needle is used, the inside diameter of which at the dispensing opening is smaller than 1 mm and is preferably between 0.5 and 0.8 mm. For total volumes of up to 1 ml they are suitable sizes for the dispensing opening of the metering needle. Smaller openings would prevent optimum flow of the liquids therethrough. Larger openings would reduce swirl formation at the edge of the dispensing opening and thus result in worse mixing.

Another suitable method is one in which a metering needle is used, the tip of which is substantially bevelled. When dispensing liquids from a metering needle with a bevelled tip into liquids which are already present, swirl effects are produced, which promote the mixing action of the method.

Another suitable method is one in which a metering needle with a closed tip is used, in which there are laterally a plurality of dispensing openings. By the provision of lateral dispensing openings, the liquid is dispensed to the side and there produces additional turbulence effects. That also promotes the mixing action of the method.

A particularly preferred method is one in which a measuring cuvette is used as the sample vessel. Particularly when carrying out analytical test reactions it is appropriate for the operation of mixing the liquids to be carried out directly in the measuring cuvette as that avoids a further automation step and further liquid transfer. That on the one hand leads to a reduction in cost and on the other hand reduces the risk of contamination. Using a measuring cuvette as the sample vessel is also possible in this measuring method for the reason that it prevents air bubbles from being formed or remaining within the liquid and the metering needle does not touch the sample vessel at any location and as a result the measuring cuvette is not subjected to mechanical stressing.

Further features and advantages of the method according to the invention will be apparent from the description hereinafter of the Figures.

Figure 2:
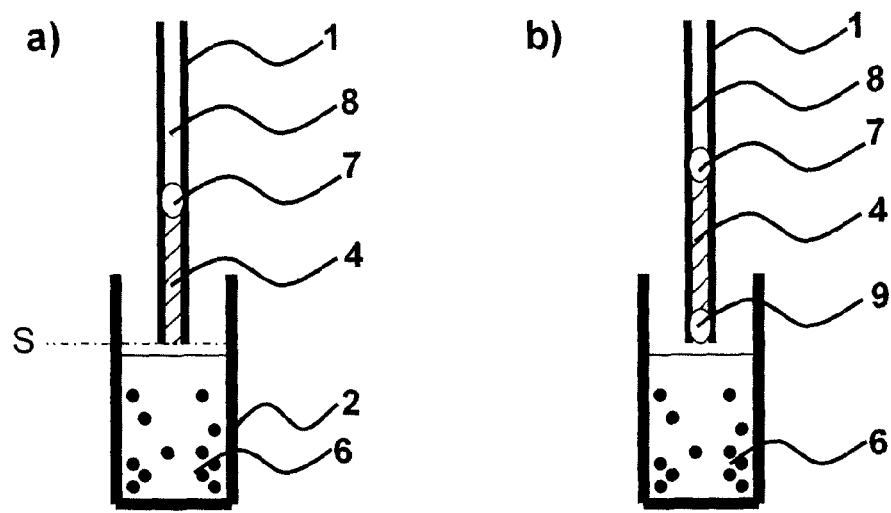

FIG. 1 shows a diagrammatic view of the method of metering and mixing liquids comprising the steps:
 a) a') dispensing a volume of liquid;
 b) sucking up a part of the volume of liquid in the sample vessel;
 c) displacing the metering needle in a vertical direction to the starting position (S), and
 d) d') dispensing the volume of liquid which is sucked up, and FIG. 2 shows a diagrammatic view of the operation of sucking in a separation air bubble.

FIG. 1a) shows a sample vessel 2 with a liquid 3, to which a further liquid 4 is to be added by means of a metering needle 1. The dispensing opening of the metering needle 1 is at a starting position S. The line F denotes the maximum filling height F of the sample vessel after complete dispensing of liquid in this step. The starting position S is above the maximum filling height F. The liquid is separated from the ambient atmosphere outwardly by a separation air bubble 5. At the beginning of the addition operation, that is to say while the metering needle 1 is moved into the sample vessel 2, the air bubble 5 is discharged to the air and thus does not remain in the liquid in the sample vessel. Displacement of the metering needle 1 into the sample vessel 2 can be effected both by a movement of the metering needle and also by a movement of the sample vessel or a combination of those movements.

FIG. 1a') shows the metering needle 1 in the sample vessel 2 at the end of the operation of dispensing the liquid 4. The dispensing opening of the metering needle is above the bottom of the sample vessel at the end position E. Now, a mixture 6 consisting of the two liquids 3 and 4 is contained in the sample vessel 2. In that case the points represent distribution of the liquid 3 within the mixture 6. In this embodiment the liquid 4 was not dispensed completely out of the metering needle 1 into the sample vessel 2. For reasons of accuracy of dispensing, a residue of the liquid 4 remains in the metering needle 1, that residue being separated off by a separation air bubble 7 from the system liquid 8 which is above that air bubble 7 in the metering needle 1.

Although in most applications good mixing of the liquids 3 and 4 is already achieved by dispensing of the liquid 4, with simultaneous movement of the metering needle 1 into the sample vessel 2, differences in concentration can still prevail in the sample vessel 2, depending on the respective nature of the liquids. For that reason a part of the liquid in the sample vessel is sucked up and dispensed again, in a further step. FIG. 1b) shows the metering needle 1 after the operation of sucking up a part of the volume of liquid mixture 6, present in the sample vessel. In that case the dispensing opening of the metering needle is in the end position E.

After the operation of sucking up liquid the metering needle is moved out of the sample vessel again until the dispensing opening is at the starting position S. That is shown in FIG. 1c). A large proportion of the volume of liquid of the mixture 6 is in the metering needle 1 and can again be dispensed into the sample vessel 2 while the metering needle 1 is moved into the sample vessel 2.

FIG. 1d) shows the metering needle in the sample vessel during the renewed operation of dispensing liquid. In this case the metering needle 1 moves into the sample vessel 2 until the dispensing opening is at the end position E. At the same time the liquid is dispensed from the metering needle.

FIG. 1d') shows the end of the mixing operation. In this case, the liquid mixture 6 which is now a highly homogeneous mixture of the solutions 3 and 4 is in the sample vessel 2 and a remaining residue of the liquid 4 and a separation air bubble 7 which separates it from the system liquid 8 in the needle 1 is in the metering needle 1.

FIG. 2 shows a separation air bubble 9 being accommodated in the metering needle 1 prior to step b) in FIG. 1b) to prevent mixing of the remaining liquid 4 in the metering needle 1 with the liquid mixture 6.

FIG. 2a) shows in that respect that, after the addition of the liquid 4 to the liquid 3 in the sample vessel 2, the metering needle is moved with the dispensing opening into the starting position S. In that case the dispensing opening of the metering needle 1 is above the maximum filling height of the sample vessel after complete dispensing of liquid in this step and is thus above the surface of the liquid.

Due to air being sucked in as shown in FIG. 2b) an air bubble 9 occurs in the metering needle 1, the air bubble 9 separating off the liquid 1 in the metering needle, in the subsequent operation of sucking in the liquid mixture 6. The separation air bubble 9 is sucked in at that location in order in the subsequent step b) (FIG. 1b)) to prevent mixing of the residue of the liquid 4, which remains in the metering needle, with the liquid mixture 6 which is to be mixed. In addition the metering needle contains the air bubble 7 separating the liquid 4 from the system liquid 8.

For the purposes of the original disclosure it is pointed out that all features as can be seen by a man skilled in the art from the present description, the drawings and the claims, even if they are described in specific terms only in connection with certain other features, can be combined both individually and also in any combinations with others of the features or groups of features disclosed here insofar as that has not been expressly excluded or technical aspects make such combinations impossible or meaningless. A comprehensive explicit representation of all conceivable combinations of features is dispensed with here only for the sake of brevity and readability of the description.

The invention claimed is:

1. A method of automatically metering and mixing liquids in a sample vessel by means of a metering needle, comprising the following steps:
   a) dispensing a volume of a liquid or a plurality of volumes of a plurality of liquids from a metering needle into a sample vessel, wherein the operation of dispensing the liquid or liquids from the metering needle begins when the dispensing opening of the metering needle is at a starting position, wherein said starting position is disposed in a vertical direction at a spacing from the bottom of the sample vessel, which corresponds to the maximum filling height of the sample vessel after complete dispensing of the liquid in this step or is above said filling height or at a maximum 10% there below, with respect to the spacing from the bottom of the sample vessel to the maximum filling height of the sample vessel after complete dispensing of the liquid in this step, the dispensing operation is continued while the metering needle is moved in a vertical direction downwardly in the direction of an end position, wherein said end position is in a vertical direction beneath said starting position and at a spacing relative to the bottom of the sample vessel, and the dispensing operation ends when the dispensing opening of the metering needle is at said end position;
   b) sucking up at least a part of the volume of liquid present in the sample vessel by means of the metering needle while the dispensing opening of the metering needle is in the end position;
   c) moving the metering needle in a vertical direction until the dispensing opening is at the starting position; and
   d) dispensing the volume of liquid which has been sucked up from the dispensing needle, wherein the dispensing operation begins when the dispensing opening of the metering needle is at the starting position, the dispensing operation is continued while the metering needle is moved in a vertical direction downwardly in the direction of the end position, and the dispensing operation ends when the dispensing opening of the metering needle is at the end position.

2. A method according to claim 1, wherein prior to step a) a volume of a liquid or a plurality of volumes of a plurality of liquids are dispensed from a metering needle into the sample vessel.

3. A method according to claim 1, wherein steps a) to d) are repeated with one or more further liquids.

4. A method according to claim 1, wherein steps b) to d) are repeated one or more further times.

5. A method according to claim 1 wherein the starting position is in a vertical direction at a spacing above the maximum filling height after complete dispensing of the liquid in the respective step, of between 0.5% and 50%, preferably between 0.5% and 20%, particularly preferably between 0.5% and 10%, with respect to the spacing from the bottom of the sample vessel to the maximum filling height of the sample vessel after complete dispensing of the liquid in the respective step.

6. A method according to claim 1, wherein the end position is in a vertical direction at a spacing above the bottom of the sample vessel, of between 0.5% and 20%, preferably between 0.5% and 10%, particularly preferably between 0.5% and 5%, with respect to the spacing from the bottom of the sample vessel to the maximum filling height of the sample vessel after complete dispensing of liquid in the respective step.

7. A method according to claim 1, wherein a plurality of liquid volumes are separated in the metering needle by air bubbles.

8. A method according to claim 1, wherein before step b) the metering needle is displaced in a vertical direction upwardly until the dispensing opening is above the surface of the liquid, then a separation air bubble is sucked in and then the metering needle is moved into the end position again.

9. A method according to claim 1, wherein the speed at which the metering needle is moved into the sample vessel is proportional to the speed of dispensing of the liquid or liquids.

10. A method according to claim 1, wherein the speed at which the metering needle is moved into the sample vessel remains constant.

11. A method according to claim 1, wherein the speed of dispensing of the liquid or liquids from the metering needle remains constant.

12. A method according to claim 1, wherein the speed of dispensing of the liquid or liquids from the metering needle is between 0.1 and 2 ml/s, preferably between 0.2 and 1 ml/s.

13. A method according to claim 1, wherein in step b) 50-100% by volume of the volume of liquid present in the sample vessel, preferably 70-95% by volume, particularly preferably 90-95% by volume, is sucked up.

14. A method according to claim 1, wherein the metering needle is heated for temperature control of the liquids.

15. A method according to claim 1, wherein a metering needle is used, the inside diameter of which at the dispensing opening is smaller than 1 mm and is preferably between 0.5 and 0.8 mm.

16. A method according to claim 1, wherein a needle with a beveled tip is used as the metering needle.

17. A method according to claim 1, wherein a needle with a closed tip, in which a plurality of dispensing openings are laterally provided, is used as the metering needle.

18. A method according to claim 1, wherein a measuring cuvette is used as the sample vessel.

19. A method according to claim 1, wherein a plurality of metering needles are used to simultaneously fill a plurality of sample vessels.

20. A method of automatically metering and mixing liquids in a sample vessel by means of a metering needle, comprising the following steps:
   a) dispensing a volume of a liquid or a plurality of volumes of a plurality of liquids from a metering needle into a sample vessel containing a liquid having a surface, wherein the operation of dispensing the liquid or liquids from the metering needle begins when the dispensing opening of the metering needle is at a starting position above said surface of said contained liquid, the dispensing operation is continued while the metering needle is moved in a vertical direction downwardly in the direction of an end position beneath said surface of said contained liquid, and the dispensing operation ends when the dispensing opening of the metering needle is at said end position, wherein the starting position is disposed in a vertical direction at a spacing from the bottom of the sample vessel, which corresponds to the maximum filling height of the sample vessel after complete dispensing of the liquid in this step or is above said filling height or at a maximum 10% there below, with respect to the spacing from the bottom of the sample vessel to the maximum filling height of the sample vessel after complete dispensing of the liquid in this step, and wherein the end position is in a vertical direction beneath the starting position and at a spacing relative to the bottom of the sample vessel;
   b) sucking up at least a part of the volume of liquid present in the sample vessel by means of the metering needle while the dispensing opening of the metering needle is in the end position;
   c) moving the metering needle in a vertical direction until the dispensing opening is at the starting position; and
   d) dispensing the volume of liquid which has been sucked up from the dispensing needle, wherein the dispensing operation begins when the dispensing opening of the metering needle is at the starting position, the dispensing operation is continued while the metering needle is moved in a vertical direction downwardly in the direction of the end position, and the dispensing operation ends when the dispensing opening of the metering needle is at the end position.

* * * * *